United States Patent [19]

Cheung et al.

[11] Patent Number: 5,510,550
[45] Date of Patent: Apr. 23, 1996

[54] SELECTIVE ACETYLENE HYDROGENATION

[75] Inventors: Tin-Tack P. Cheung; Marvin M. Johnson; Scott H. Brown; Stan A. Zisman; James B. Kimble, all of Bartlesville, Okla.

[73] Assignee: Phillips Petroleum Company, Bartlesville, Okla.

[21] Appl. No.: 445,441

[22] Filed: May 19, 1995

Related U.S. Application Data

[62] Division of Ser. No. 269,723, Jul. 1, 1994.

[51] Int. Cl.$^6$ ............................... C07C 5/08; C07C 7/67
[52] U.S. Cl. .................. 585/259; 585/260; 585/261; 585/262; 585/500; 585/601
[58] Field of Search ........................ 585/259, 260, 585/261, 262, 500, 601

[56] References Cited

U.S. PATENT DOCUMENTS

| | | |
|---|---|---|
| 3,325,556 | 6/1967 | De Rosset . |
| 3,477,962 | 11/1969 | Kardys . |
| 3,489,809 | 1/1970 | Keith et al. . |
| 3,816,344 | 6/1974 | Shimizu et al. . |
| 4,009,126 | 2/1977 | McFarland . |
| 4,226,809 | 10/1980 | Shioyama . |
| 4,404,124 | 9/1983 | Johnson et al. . |
| 4,484,015 | 11/1984 | Johnson et al. ................... 585/262 |
| 4,513,159 | 4/1985 | McFarland ........................ 585/625 |
| 4,547,600 | 10/1985 | Cosyns et al. .................... 585/259 |
| 4,644,088 | 2/1987 | McFarland ........................ 585/658 |
| 4,658,080 | 4/1987 | McFarland ........................ 585/658 |
| 4,839,329 | 6/1989 | Ihm et al. ......................... 502/339 |
| 4,906,602 | 3/1990 | Schneider et al. ................ 502/304 |
| 5,032,565 | 7/1991 | Berrebi ............................ 502/331 |
| 5,059,731 | 10/1991 | Berrebi ............................ 585/259 |
| 5,068,477 | 11/1991 | Berrebi ............................ 585/274 |

OTHER PUBLICATIONS

Yeung H. Park and Geoffrey L. Price, "Promotional Effects of Potassium on Pd/Al$_2$O$_3$ Selective Hydrogenation Catalysts", Ind. Eng. Chem. Res. 1992, vol. 31, pp. 469–474.

*Primary Examiner*—E. Rollins Cross
*Assistant Examiner*—E. D. Irzinski
*Attorney, Agent, or Firm*—K. K. Brandes

[57] ABSTRACT

A catalyst composition comprising palladium, silver and a support material (preferably alumina) is contacted at a relatively low temperature (of up to about 60° C.) with a liquid composition comprising an effective reducing agent (preferably an alkali metal borohydride, hydrazinc, formaldehyde, formic acid, ascorbic acid, dextrose, aluminum powder). Preferably, at least one alkali metal compound (more preferably KOH, RbOH, CsOH, KF) is also present in the liquid composition. An improved process for selectively hydrogenating acetylene (to ethylene) employs this wet-reduced catalyst composition.

26 Claims, No Drawings

SELECTIVE ACETYLENE HYDROGENATION

This application is a division of U.S. patent application Ser. No. 08/269,723, filed Jul. 1, 1994.

BACKGROUND OF THE INVENTION

In one aspect, this invention relates to a method of making supported palladium/silver compositions exhibiting improved acetylene hydrogenation catalyst performance. In another aspect, this invention relates to a process for selectively hydrogenating acetylene to ethylene employing supported palladium/silver catalysts having been prepared by the preparation method of this invention.

The selective hydrogenation of acetylene being present as an impurity in monoolefin-containing streams (e.g., ethylene streams from thermal ethane crackers) is commercially carried out with an alumina-supported palladium/silver catalyst, substantially in accordance with the disclosure in U.S. Pat. No. 4,404,124 and its division, U.S. Pat. No. 4,484,015. The operating temperature for this process is selected such that essentially all acetylene is hydrogenated to ethylene (and thus removed from the feed stream) while only an insignificant amount of ethylene is hydrogenated to ethane (to minimize ethylene losses and to avoid a "runaway" reaction which is difficult to control, as has been pointed out in the above-identified patents). The selective acetylene hydrogenation process can be most effectively controlled when there is a large difference between the temperature at which essentially all acetylene is hydrogenated and a higher temperature at which excessive ethylene-to-ethane conversion occurs. Even though the $Pd/Ag/Al_2O_3$ catalyst described in the above-identified patents is an excellent catalyst, the present invention represents an improvement in the preparation of this catalyst and related catalysts and their use for the selective acetylene hydrogenation.

SUMMARY OF THE INVENTION

It is an object of this invention to prepare improved palladium/silver-containing catalyst compositions which are useful for catalyzing the selective hydrogenation of acetylene to ethylene. It is another object of this invention to carry out the selective hydrogenation of acetylene to ethylene in the presence of improved palladium/silver catalysts. It is a further object of this invention to employ these improved catalysts for hydrogenating acetylene which is present in small amounts in ethylene-containing streams. Other objects and advantages will be apparent from the detailed description and appended claims.

In accordance with this invention, a preparation method comprises contacting a solid composition (also referred to as "base catalyst composition" or "starting catalyst composition") comprising palladium, silver and an inorganic support material with a liquid composition comprising at least one effective reducing agent at a temperature of up to about 60° C., at contacting conditions which are effective in enhancing the selectivity of said solid catalyst composition when employed as a catalyst for hydrogenating acetylene to ethylene. In a preferred embodiment, said contacting is carried out with a reducing agent in the presence of at least one alkali metal compound, more preferably an alkali metal hydroxide and/or an alkali metal fluoride.

In one specific embodiment, the starting catalyst composition is reduced with a solution of an alkali metal borohydride, dried and then heated (preferably in an oxidizing gas atmosphere) at a temperature in the range of about 300° C. to about 700° C. for at least about 10 minutes. In another specific embodiment, the starting catalyst composition is reduced with a solution of hydrazine and dried, and, optionally, thereafter heated (preferably in an oxidizing gas atmosphere) at a temperature in the range of about 300° C. to about 700° C. for at least about 10 minutes. In a further specific embodiment, the starting catalyst composition is reduced with a solution containing formaldehyde and/or alkali metal fluoride and at least one alkali metal hydroxide and dried and, preferably, thereafter heated (preferably in an oxidizing gas atmosphere) at a temperature in the range of about 300° C. to about 700° C. for at least about 10 minutes. In still another specific embodiment, the starting catalyst composition is reduced with a solution containing dextrose, and at least one alkali metal hydroxide, dried and thereafter heated (preferably in an oxidizing gas atmosphere) at a temperature of about 300° C. to about 700° C. for at least about 10 minutes.

Also in accordance with this invention, catalyst compositions prepared by the above-described methods are provided.

Further in accordance with this invention, a process for selectively hydrogenating acetylene (preferably present in a small amount in an ethylene-containing gas stream) with hydrogen gas to ethylene is carried out with a catalyst prepared by one of the above described methods of this invention.

DETAILED DESCRIPTION OF THE INVENTION

The starting material (also referred to as "base catalyst") which is wet-reduced in accordance with this invention can be any supported palladium- and silver-containing catalyst composition. This catalyst composition can be fresh (e.g., supplied by United Catalysts, Inc., Louisville, Ky., under the product designation of "G-83C") or it can be a used and thereafter oxidatively regenerated catalyst composition. The base catalyst can contain any suitable solid support material. Preferably, the support material is selected from the group consisting of alumina (more preferably alpha-alumina), titania, zirconia and mixtures thereof. Presently most preferred is the palladium/silver/alumina composition described in U.S. Pat. No. 4,404,124, the disclosure of which is incorporated herein by reference. This skin-type catalyst generally contains about 0.01–1 (preferably about 0.01–0.2) weight-% palladium and about 0.01–10 (preferably about 0.02–2) weight-% silver, at a Ag:Pd weight ratio of about 1:1 to about 10:1, more preferably about 5:1 to about 8:1. The particle size of the supported Pd/Ag base catalyst generally is about 1–10 mm, most preferably 2–6 mm. The supported Pd/Ag base catalyst particles can have any suitable shape, and preferably are spheres or cylindrical pellets. Generally, the surface area of the supported Pd/Ag base catalyst (determined by the BET method employing $N_2$) is about 1–100 $m^2/g$.

The above-described base catalyst particles are contacted with a reduction composition (hereinafter referred to as "wet-reduction composition"), which contains at least one reducing agent and, if the reducing agent is not liquid, also at least one liquid component, in accordance with this invention. Suitable reducing agents include (but are not limited to) alkali metal borohydrides (such as $NaBH_4$, $KBH_4$), hydrazine, aldehydes containing 1–6 carbon atoms per molecule (preferably formaldehyde), ketones containing 1–6 carbon atoms per molecule, carboxylic acids containing 1–6 carbon atoms per molecule (preferably, formic acid, ascorbic acid), reducing sugars which contain an aldehyde group or, alternatively, an α-hydroxyketone group (preferably dextrose), aluminum metal (preferably powder), zinc metal (preferably powder), and the like, and mixtures thereof. In the case of the above-listed aldehydes, ketones, carboxylic acids, reducing sugars, zinc metal, and aluminum metal, these reducing agents are most effective when an alkaline agent (preferably an alkali metal hydroxide and/or fluoride) is also present in the wet-reduction composition. When the reducing agent is a solid (e.g., Al powder), a liquid substance which functions as a solvent or, alternatively, as a dispersing medium is also present in the wet-reduction composition. Water or a lower aliphatic alcohol (in particular methanol), or mixtures thereof can serve as the non-reducing liquid component. Generally, the weight percentage of the at least one reducing agent in the wet reduction composition is in the range of about 0.5 to about 50 weight-%, but may be even higher. Preferably, the pH of the wet-reduction composition, in particular if it is aqueous, is about 8–14.

In a particularly preferred embodiment of this invention, the wet-reduction composition additionally contains at least one dissolved compound of at least one alkali metal (preferably selected from the group consisting of potassium, rubidium and cesium). Presently preferred alkali metal compounds are halides, hydroxides, carbonates, bicarbonates, nitrates, carboxylates (such as acetates, oxalates, citrates and the like). Fluorides and hydroxides of potassium, rubidium and cesium are particularly preferred, especially when the reducing agent is an aldehyde or ketone or carboxylic acid or reducing sugar or zinc or aluminum. Generally, the concentration of the alkali metal compound in the wet-reduction composition and the weight ratio of alkali metal compound to the base catalyst composition are chosen so as to incorporate about 0.05–5 weight-% alkali metal (on an elemental basis) into the catalyst composition. It is also possible to carry out the contacting of the catalyst composition with at least one dissolved alkali metal compound before the wet-reduction or, alternatively, after the wet-reduction has occurred. However, the essentially simultaneous wet-reduction and treatment with at least one alkali metal compound, as described above, is the presently preferred method. It is, of course, also possible (yet presently not preferred) to carry out the contacting with the alkali metal compound(s) both before said wet-reduction and concurrently with said wet-reduction, or both concurrently with said wet-reduction and after said wet-reduction, or before, concurrently with and after said wet-reduction.

The contacting of the supported Pd/Ag base catalyst composition with the wet reduction composition can be carried out in any suitable manner. In general, the catalyst composition and the wet-reduction composition are contacted (mixed) for a time period of at least about 1 second, preferably about 10 seconds to about 10 hours, at a relatively low temperature of about 10°–60° C. More preferably, the time period is about 0.02 to about 2 hours, and the temperature is in the range of about 20° C. to about 50° C. The pressure during the wet-reduction step is approximately atmospheric (about 0 psig). This contacting step can be carried out as a batch-type operation (mixing or soaking) or continuously (e.g., by using a mixing screw or a static mixer equipped with internal baffles or by spraying the base catalyst composition which is placed on a moving conveyer belt with the wet-reduction composition).

The wet-reduced catalyst composition is then substantially separated from the wet-reduction composition by any conventional solid-liquid separation technique, such as filtering (presently preferred), decanting of the liquid, centrifuging, and the like. Thereafter, the substantially separated, wet-reduced catalyst composition is dried, generally for a time period of about 0.2–20 hours (preferably about 2–6 hours), at a temperature of about 50°–150° C. (preferably about 100°–130° C.). It is preferred to then heat (calcine) the dried, wet-reduced catalyst composition, generally for a time period of about 0.2–20 hours (preferably about 1–6 hours) at a temperature of about 300°–700° C. (preferably about 400°–600° C.). Both the drying step and the calcining step can be carried out in an oxidizing (i.e., $O_2$-containing) gas atmosphere or in an inert gas atmosphere (e.g., under $N_2$, He, Ar, and the like), preferably in air. This calcining step is particularly preferred when an alkali metal hydroxide has been used as the reducing agent.

The thus-prepared catalyst composition which has been dried and, optionally, calcined can then be employed in a process for hydrogenating acetylene to primarily ethylene. Optionally, the catalyst is first contacted, prior to the acetylene hydrogenation, with hydrogen gas or with a gaseous hydrocarbon generally at a temperature in the range of about 30° C. to about 100° C., for a time period of about 4 to about 20 hours. During this contacting with $H_2$ or hydrocarbon(s) before the selective acetylene hydrogenation commences, palladium and silver compounds (primarily oxides) which may be present in the wet-reduced catalyst composition after the drying step and the optional calcining step (described above) are substantially reduced to palladium and silver metal. When this optional reducing step is not carried out, the hydrogen gas present in the reaction mixture accomplishes this reduction of oxides of Pd and Ag during the initial phase of the acetylene hydrogenation reaction of this invention.

The selective hydrogenation process of this invention is carried out by contacting (a) a feed gas which comprises acetylene, preferably an ethylene stream containing acetylene as an impurity (generally at a level of about 1 ppm to about 50,000 ppm $C_2H_2$) and (b) hydrogen gas with (c) the catalyst composition(s) of the present invention. In order to best attain substantially complete removal of the acetylene, there should be at least one mole of hydrogen for each mole of acetylene present. Gases (a) and (b) are generally premixed before their contact with the catalyst composition (c). It is within the scope of this invention to have additional gases (such as methane, ethane, propane, propene, butane, butenes, carbon monoxide, hydrogen sulfide) present in the feed gas, as long as they do not significantly interfere with the selective hydrogenation of acetylene to ethylene. Generally, CO and $H_2S$ are present in trace amounts (preferably less than about 0.5 weight percent CO and less than about 50 ppm $H_2S$).

The temperature necessary for the selective hydrogenation of acetylene to ethylene depends largely upon the activity of the catalysts and the extent of acetylene removal desired. Generally, temperatures in the range of about 0° C. to about 150° C. are used. Any suitable reaction pressure can be employed. Generally, the total pressure is in the range of about 100 to about 1,000 pounds per square inch gauge (psig). The gas hourly space velocity (GHSV) can also vary over a wide range. Typically, the space velocity will be in the range of about 1,000 to about 10,000 $m^3$ of feed per $m^3$ of catalyst per hour, more preferably about 2,000 to about 8,000 $m^3/m^3$/hour.

Regeneration of the catalyst composition can be accomplished by heating the catalyst composition in air (at a temperature which preferably does not exceed about 700 °

C.) to burn off any organic matter and/or char that has been accumulated on the catalyst composition. Optionally, the oxidatively regenerated composition is reduced with $H_2$ or a suitable hydrocarbon (as has been described above) before its redeployment in the selective hydrogenation of acetylene. It is also within the scope of this invention to treat the oxidatively regenerated catalyst composition with a wet-reduction composition, followed by a drying step and an optional calcining step (i.e., in accordance with the method of this invention) before the catalyst is redeployed in the selective hydrogenation of acetylene (either directly or after reduction with $H_2$ or a suitable hydrocarbon, as has been described above).

The following examples are presented to further illustrate this invention and are not to be construed as unduly limiting its scope.

Example I

This example illustrates the reduction of supported palladium catalysts with a dissolved alkali metal borohydride and the use of this "wet-reduced" catalyst for the selective hydrogenation of acetylene to ethylene.

Catalyst A1 (Control) was a commercial $Pd/Al_2O_3$ catalyst which contained 0.018 weight-% Pd and about 99 weight-% alumina. It had a surface area (determined by the BET method employing $N_2$) of 3–5 $m^2/g$, and had been provided by United Catalysts Inc. (UCI), Louisville, Ky. under the product designation "G-83A".

Catalyst A2 (Control) was prepared by soaking 20 cc of Catalyst A1 in 150 cc distilled water (which had been deaerated by bubbling $N_2$ gas through), adding 0.130 grams of $NaBH_4$ to the catalyst/water mixture, and stirring the entire mixture (containing the catalyst, water and $NaBH_4$) for about 1 hour at room temperature. Then the excess liquid was drained and the soaked catalyst was washed several times with deaerated water. The wet catalyst was heated in a hydrogen gas atmosphere at 90° C. for 2 hours, and allowed to cool to room temperature under flowing $H_2$.

Catalyst A3 (Control) was prepared by soaking 23.65 grams of Catalyst A1 in 100 cc of methanol (which had been deaerated with flowing $N_2$), adding about 1 gram of solid $NaBH_4$ to the catalyst/methanol mixture, stirring the entire mixture (containing the catalyst, methanol and $NaBH_4$) for about 1 hour at room temperature, draining excess liquid, washing the soaked catalyst three times with fresh methanol, drying the washed catalyst at 180° F. (82° C.) overnight, and calcining the dried catalyst in 370° C. for about 4 hours.

Catalyst B1 (Control) was a commercial $Pd/Ag/Al_2O_3$ catalyst which contained 0.023 weight-% Pd, 0.065 weight-% Ag and about 99 weight-% alumina. It had a $BET/N_2$ surface area of 3–5 $m^2/g$, had been prepared substantially in accordance with the method described in U.S. Pat. No. 4,404,124 (column 4, lines 32–45), and had been provided by UCI (identified above) under the product designation "G-83C".

Catalyst B2 (Invention) was prepared by soaking about 20 cc of Catalyst B1 in 150 cc of deaerated methanol, adding about 1.0 gram of solid $NaBH_4$ to the catalyst/methanol mixture, stirring the entire mixture (containing the catalyst, methanol and $NaBH_4$) for about 90 minutes at room temperature, draining excess liquid, washing the soaked catalyst three times with deaerated methanol, and drying the washed catalyst under vacuum conditions.

Catalyst B3 (Invention) was prepared by soaking 20 cc of Catalyst B1 in 100 cc deaerated methanol, adding about 1.0 gram of solid $NaBH_4$ to the catalyst/methanol mixture, stirring the entire mixture (containing the catalyst, methanol and $NaBH_4$) for about 1 hour at room temperature, draining excess liquid, washing the soaked catalyst three times with deaerated methanol, drying the washed catalyst overnight at 180° F. (82°), and calcining the dry catalyst at 370° C. in air for about 3 hours.

Catalyst B4 (Invention) was prepared by calcining Catalyst B2 after it had been tested for its acetylene hydrogenation performance at 370° C. in air for about 4 hours.

About 20 cc of each of the above-described catalysts was placed into a stainless steel reactor tube having a 0.5 inch inner diameter and a length of about 18 inches. Each catalyst was treated with flowing hydrogen gas under a pressure of 200 psig, at a temperature of about 110°–130° F., for about 16 hours. Thereafter, the reactor tube was cooled to about 110° F., and a hydrocarbon-containing feed gas containing 1.98 weight-% hydrogen, 21.40 weight-% methane, 21.18 weight-% ethane, 55.09 weight-% ethylene, 0.35 weight-% acetylene and 0.03 weight-% carbon monoxide was introduced into the reactor tube at a rate of about 900 cc/minute. The reactor temperature was gradually increased to the desired reaction temperature, and samples of the formed product were analyzed by means of a gas chromatograph at various time intervals.

Two key test results are summarized in Table I: $T_1$, which is the "cleanup" temperature at which acetylene is substantially hydrogenated to ethylene (so as to obtain a product containing less than about 10 ppm (ppm=parts per million parts by weight) of acetylene; and $T_2$, which is the "runaway" temperature at which a substantial portion of ethylene is converted to ethane (exothermic "runaway" reaction) and the ethylene/ethane molar ratio in the product has decreased to about 2.3 (from about 2.8 attained at lower temperatures). The higher the temperature difference ($T_1-T_2$) attained with a particular catalyst, the more satisfactorily will this catalyst perform as a selective acetylene hydrogenation catalyst. Test results are summarized in Table I.

TABLE I

| Run | Catalyst | $T_1$ (°F.) | $T_2$ (°F.) | $T_2-T_1$ |
|---|---|---|---|---|
| 1 (Control) | A1 ($Pd/Al_2O_3$, not wet-reduced) | 114 | 143 | 29 |
| 2 (Control) | A2 ($Pd/Al_2O_3$, wet-reduced with $NaBH_4$) | 116 | 145 | 29 |
| 3 (Control) | A3 ($Pd/Al_2O_3$, wet-reduced with $NaBH_4$, and calcined) | 133 | 164 | 31 |
| 4 (Control) | B1 ($Pd/Ag/Al_2O_3$, not wet-reduced) | 120 | 155 | 35 |
| 5 (Invention) | B2 ($Pd/Ag/Al_2O_3$, wet-reduced with $NaBH_4$) | 192 | 232 | 40 |
| 6 (Invention) | B3 ($Pd/Ag/Al_2O_3$, wet-reduced with $NaBH_4$, and calcined) | 134 | 183 | 49 |
| 7 (Invention) | B4 ($Pd/Ag/Al_2O_3$, wet-reduced with $NaBH_4$, and calcined) | 141 | 190 | 49 |

Test results in Table I show that wet-reduction of a $Pd/Al_2O_3$ catalyst with dissolved sodium borohydride, either with or without subsequent calcination, had no significant effect on $T_2-T_1$ (i.e., the temperature difference defined above). On the other hand, the wet-reduction of the $Pd/Ag/Al_2O_3$ catalyst resulted in an enhanced temperature difference, in particular when calcination in air was carried out after the wet-reduction. The presence of traces of formed $C_4$ hydrocarbons (about 0.02 weight-%) in the hydrogenation product was observed.

Example II

This example illustrates the wet-reduction of a supported palladium/silver catalyst with dissolved hydrazine in accordance with this invention.

Catalyst C1 (Control) was substantially the same as Catalyst B1 described in Example I.

Catalyst C2 (Invention) was prepared by soaking 23.3 grams of Catalyst C1 with a solution of 5 cc $N_2H_4 \cdot H_2O$ in 45 cc of distilled water for about 1 hour. The excess liquid was poured off, and the wet catalyst was heated in a forced air convection oven at 125° C. for about 4 hours.

Both catalysts were tested for their selective acetylene hydrogenation activity, substantially in accordance with the procedure described in Example I, except that the hydrocarbon-containing feed contained about 33.2 weight-% methane, about 0.08 weight-% ethane, about 63.1 weight-% ethylene, about 0.35 weight-% acetylene about 0.05 weight-% carbon monoxide, and about 3.2 weight-% $H_2$. Test results are summarized in Table II.

TABLE II

| Run | Catalyst | $T_1$ (°F.) | $T_2$ (°F.) | $T_2-T_1$ | ppm Ethane Formed at $T_1$ |
|---|---|---|---|---|---|
| 8 (Control) | C1 (Pd/Ag/Al$_2$O$_3$, not wet-reduced | 107 | 145 | 38 | 2970 |
| 9 (Invention) | C2 (Pd/Ag/Al$_2$O$_3$, wet-reduced with N$_2$H$_4$) | 123 | 166 | 43 | 2290 |

Test data in Table II show that wet-reduction of a Pd/Ag/Al$_2$O$_3$ catalyst was beneficial in terms of increasing the temperature difference $T_2-T_1$ (defined in Example I). The presence of trace amounts of formed butenes (0.03–0.05 weight-%) the hydrogenation product was observed.

Table II also presents test data on the amount (in ppm by weight) of ethane produced at the "cleanup" temperature, $T_1$, which is a measure of the selectivity to ethylene exhibited by a particular catalyst at the "cleanup" temperature (defined in Example I). These test data were obtained by subtracting the amount of ethane present in the feed from the amount of ethane present in the hydrogenation product produced at $T_1$. Table II clearly shows that less of the undesirable ethane was formed with the wet-reduced catalyst, $C_2$ (as compared with the untreated Catalyst $C_1$). Consequently, more desirable ethylene was produced with the invention Catalyst $C_2$ (as compared with the untreated Catalyst $C_1$).

Example III

This example illustrates the wet reduction of a Pd/Ag/Al$_2$O$_3$ with formaldehyde in the presence of an alkali metal hydroxide, in accordance with this invention.

Catalyst D1 (Invention) was prepared by mixing 20 cc of control Catalyst B1 (described in Example I) with about 110 cc of a solution which contained about 38 weight-% formaldehyde, about 12 weight-% methanol and about 50 weight-% water, and 1.13 grams of NaOH. The entire mixture was stirred at room temperature for about 2 hours, excess liquid was poured off, the soaked catalyst was rinsed three times with fresh methanol, the washed catalyst was dried overnight at about 88° C., and the dried catalyst was then calcined in air at 370° C. for 4.5 hours.

Catalyst D2 (Invention) was prepared by mixing 20 cc of control Catalyst C1 (described in Example II) with 110 cc of a solution, which contained about 37 weight-% formaldehyde, about 17 weight-% methanol and about 46 weight-% water, and 1.18 grams of NaOH. The entire mixture was stirred at room temperature for about 2 hours. Excess liquid was poured off. The wet catalyst was rinsed three time with 150 cc of fresh methanol, and dried under $H_2$ at 60°–100° C. for several hours.

Catalyst D3 (Invention) was prepared by mixing 20 cc of Catalyst C1 with 75 cc of a solution, which contained about 37 weight-% formaldehyde, about 17 weight-% methanol and about 46 weight-% water, and about 0.6 gram of KOH. The entire mixture was stirred at room temperature for about 40 minutes, excess liquid was poured off, the wet catalyst was dried at about 88° C., and was then calcined at 200° C. for several hours.

The thus-prepared catalysts were tested for the selective acetylene hydrogenation activity, substantially in accordance with the procedure described in Example I. The hydrocarbon-containing feed had essentially the same composition as the feed employed in the tests of Example I. Test results for the three catalysts described in this Example are summarized in Table III. Also included in this table are the test results from control Run 4 (see Table I) employing control Catalyst B1 (for comparison with Run 10 employing invention Catalyst D1). Results from another control run (Run 11 employing Catalyst C1) is listed for comparison with invention Catalysts D2 and D3 (Runs 12 and 13).

TABLE III

| Run | Catalyst | $T_1$ (°F.) | $T_2$ (°F.) | $T_2-T_1$ |
|---|---|---|---|---|
| 4 (Control) | B1 (Pd/Ag/Al$_2$O$_3$, not wet-reduced) | 120 | 155 | 35 |
| 10 (Invention) | D1 (Pd/Ag/Al$_2$O$_3$, wet-reduced with CH$_2$O in presence of NaOH, and calcined) | 125 | 171 | 46 |
| 11 (Control) | C1 (Pd/Ag/Al$_2$O$_3$, not wet-reduced) | 134 | 167 | 33 |
| 12 (Invention) | D2 (Pd/Ag/Al$_2$O$_3$, wet-reduced with CH$_2$O in presence of NaOH), | 129 | 182 | 53 |
| 13 (Invention) | D3 (Pd/Ag/Al$_2$O$_3$, wet-reduced with CH$_2$O in presence of KOH, and calcined) | 143 | 209 | 66 |

Test results in Table III clearly show that wet-reduction of a Pd/Ag/Al$_2$O$_3$ catalyst with formaldehyde in the presence of an alkali metal hydroxide (with or without subsequent calcination) was quite effective in increasing the temperature difference $T_2-T_1$ (defined in Example I). The presence of trace amounts of $C_4$ hydrocarbons (0.01–0.02 weight-%) in the hydrogenation product was observed.

Example IV

This example illustrates the wet-reduction of supported palladium catalysts with formaldehyde in the presence of alkali metal compounds and the performance of these materials as catalysts in the selective hydrogenation of acetylene.

Catalyst E1 (Control) was a commercial "G-83A" $Pd/Al_2O_3$ catalyst, described in Example I (Catalyst A1).

Catalyst E2 (Control) was prepared by soaking, with occasional stirring, 30 grams of Catalyst E1 with a solution of 0.42 gram of 88 weight-% KOH pellets in 26 grams of distilled water for about 1 hour at room temperature, followed by draining excess solution, drying for 16 hours at 125° C., and calcining in air for 2 hours at 1000° F. (538° C.).

Catalyst E3 (Control) was prepared in accordance with the procedure for Catalyst E2, except that Catalyst E1 was soaked with a mixture of 0.42 gram of 88% KOH pellets and 26 grams of a commercially available formaldehyde solution containing 38 weight-% $CH_2O$, 12 weight-% $CH_3OH$ and 50 weight-% $H_2O$.

Catalyst E4 (Control) was a commercial "G-83C" $Pd/Ag/Al_2O_3$ catalyst described in Example I (Catalyst B1).

Catalyst E5 (Control) was prepared by soaking, with occasional stirring, 30 grams of Catalyst E4 with a solution of 0.48 gram of 88% KOH pellets in 26 grams of water for about 1 hour at room temperature, followed by draining excess solution, drying for 8 hours at 125° C., and calcining in air for 2 hours at 1000° F. (538° C.).

Catalyst E6 (Invention) was prepared in accordance with the procedure for Catalyst E5, except that Catalyst E4 was soaked with a mixture of 0.48 gram of 88% KOH pellets and 26 grams of the above-described formaldehyde solution.

Catalysts E1 through E6 were tested substantially in accordance with the procedure described in Example I. Each catalyst had been preheated for 1 hour with flowing hydrogen gas at 100° F./200 psig and then for 1 hour with the hydrocarbon-containing feed (containing methane, ethane, ethylene, acetylene, carbon monoxide and hydrogen; similar to the feed described in Example II) at 100° F./200 psig. Thereafter, the temperature was gradually raised while the feed passed through the reactor. Test results are summarized in Table IV.

Test data in Table IV show that wet-reduction of a $Pd/Al_2O_3$ catalyst (without Ag) with formaldehyde in the presence of an alkali metal compound (KOH) showed no improvement (in terms of $T_2-T_1$ and of ethane formed at $T_1$) over treatment with KOH alone (compare Run 16 with Run 15). In contrast, wet-reduction of a $Pd/Ag/Al_2O_3$ catalyst with formaldehyde in the presence of KOH in accordance with this invention resulted in a significant increase in $T_2-T_1$ and also in a significant decrease of ethane formed at $T_1$ (compare Run 19 with Run 18).

Example V

This example further illustrates a particularly preferred feature of this invention: wet-reduction of $Pd/Ag/Al_2O_3$ catalysts with formaldehyde in the presence of alkali metal compounds.

Catalyst F1 (Control) was a commercial "G-83C" $Pd/Ag/Al_2O_3$ catalyst (essentially the same as Catalyst B1, Example I).

Catalyst F2 (Control) was a "G-83C" $Pd/Ag/Al_2O_3$ catalyst (defined above) which had been used for the selective hydrogenation of acetylene to ethylene in a Texas refinery of Phillips Petroleum Company, and had then been regenerated by heating it in air to a temperature of 1000° F. within a time period of 3 hours, followed by calcining in air at that temperature for 4 hours. Thereafter, the calcined, used catalyst was cooled to room temperature.

Catalyst F3 (Invention) was prepared as follows 0.51 gram of 88 weight-% KOH pellets (equivalent to 0.008 mole KOH) was added to 30 grams of a 37–38 weight-% formaldehyde solution in methanol. The formed solution was stirred for about one minute, 30 grams of control Catalyst F2 (regenerated "G- 83C ") were added to the solution, and the obtained mixture was kept at room temperature for 1 hour, with occasional stirring. Then excess liquid was decanted, the soaked tablets were dried in air at 125° C. for 5 hours, and the dried tablets were calcined in air at 538° C. for 2 hours.

Catalyst F4 (Invention) was prepared essentially in accordance with the above-described procedure for Catalyst F3

TABLE IV

| Run | Catalyst | $T_1$ (°F.) | $T_2$ (°F.) | $T_2-T_1$ | ppm Ethane Formed at $T_1$ |
|---|---|---|---|---|---|
| 14 (Control) | E1 ($Pd/Al_2O_3$, not wet-reduced) | 115 | 134 | 19 | 8850 |
| 15 (Control) | E2 ($Pd/Al_2O_3$, not wet-reduced but treated with KOH, calcined) | 128 | 181 | 53 | 3400 |
| 16 (Control) | E3 ($Pd/Al_2O_3$, wet-reduced with $CH_2O$ in presence of KOH, calcined) | 135 | 186 | 51 | 3440 |
| 17 (Control) | E4 ($Pd/Ag/Al_2O_3$, not wet-reduced) | 110 | 158 | 48 | 1830 |
| 18 (Control) | E5 $Pd/Ag/Al_2O_3$, not wet-reduced but treated with KOH, calcined) | 123 | 190 | 67 | 1900 |
| 19 (Invention) | E6 $Pd/Ag/Al_2O_3$, wet-reduced with $CH_2O$ in presence of KOH, calcined) | 133 | 211 | 78 | 840 | except that 0.97 gram of 99% pure RbOH.H$_2$O (0.008 mole RbOH) was used (in lieu of 0.008 mole KOH).

Catalyst F5 (Invention) was prepared essentially in accordance with the procedure for Catalyst F3 except that 0.008 mole CsOH was used (in lieu of 0.008 mole KOH).

Catalyst: F6 (Invention) was prepared essentially in accordance with the procedure for Catalyst F3 except that Catalyst F1 (fresh "G-83C") was used as the starting material (in lieu of Catalyst F2).

Catalyst F7 (Invention) was prepared essentially in accordance with Catalyst F4 except that Catalyst F1 was used as the starting material (in lieu of Catalyst F2).

Catalyst F8 (Invention) was prepared essentially in accordance with the procedure for Catalyst F5 except that Catalyst F1 was used as the starting material (in lieu of Catalyst F2).

Catalyst F9 (Invention) was prepared essentially in accordance with the procedure for Catalyst F6 except that 0.002 mole KOH was employed (in lieu of 0.008 mole KOH).

Catalyst F10 (Invention) was prepared essentially in accordance with the procedure for Catalyst F7 except that 0.002 mole RbOH was employed (in lieu of 0.008 mole RbOH).

Catalyst F11 (Invention) was prepared essentially in accordance with the procedure for Catalyst F8 except that 0.002 mole CsOH was employed (in lieu of 0.008 mole CsOH).

Catalyst F12 (Invention) was prepared essentially in accordance with the procedure for Catalyst F6 except that 0.032 mole of KOH was employed (in lieu of 0.008 mole of KOH).

Catalyst F13 (Invention) was prepared essentially in accordance with the procedure for Catalyst F12 except that 0.032 mole of NaOH (in lieu of KOH) was employed.

Catalyst F14 (Invention) was prepared essentially in accordance with the procedure for Catalyst F3 except that 0.005 mole of KOH was employed (in lieu of 0.008 mole KOH).

Catalyst F15 (Invention) was prepared essentially in accordance with the procedure for Catalyst F3 except that 0.0275 mole of KOH was employed (in lieu of 0.008 mole KOH), the time of contact with the formaldehyde solution was only about 0.5 hour (in lieu of 1 hour), and the formaldehyde concentration was only about 18 weight-% (in lieu of 37–38%).

Catalyst F16 (Invention) was prepared essentially in accordance with the procedure for Catalyst F3 except that 0.015 mole of KOH was employed (in lieu of 0.008 mole KOH), and the formaldehyde concentration was only about 1 weight-% (in lieu of 37–38%).

Catalyst F17 (Invention) was prepared essentially in accordance with the procedure for Catalyst F3 except that 0.050 mole of KOH was employed (in lieu of 0.008 mole of KOH).

Catalyst F18 (Invention) was prepared essentially in accordance with the procedure for Catalyst F6 except that 0.05 mole of KF was employed (in lieu of 0.008 mole of KOH).

Catalyst F19 (Invention) was prepared essentially in accordance with the procedure for Catalyst F18, except that 0.007 mole of KF and 0.001 mole of KOH (in lieu of 0.008 mole KF) was employed.

Catalysts F1 through F19 were tested substantially in accordance with the procedure described in Example I, except that a hydrocarbon feed which was essentially the same as that described in Example II was employed. Test results are summarized in Table V.

TABLE V

| Run | Catalyst | $T_1$ (°F.) | $T_2$ (°F.) | $T_2-T_1$ | ppm Ethane Formed at $T_1$ |
|---|---|---|---|---|---|
| 20 (Control) | F1 (fresh (Pd/Ag/Al$_2$O$_3$, not wet-reduced) | 125 | 169 | 44 | 4320 |
| 21 (Control) | F2 (regenerated (Pd/Ag/Al$_2$O$_3$, not wet-reduced) | 139 | 176 | 37 | 3950 |
| 22 (Invention) | F3 (Pd/Ag/Al$_2$O$_3$, wet-reduced with CH$_2$O in presence of KOH) | 141 | 230 | 89 | 760 |
| 23 (Invention) | F4 (Pd/Ag/Al$_2$O$_3$, wet-reduced with CH$_2$O in presence of RbOH) | 159 | 235 | 76 | 1650 |
| 24 (Invention) | F5 (Pd/Ag/Al$_2$O$_3$, wet-reduced with CH$_2$O in presence of CsOH) | 177 | 290 | 113 | 700 |
| 25 (Invention) | F6 (Pd/Ag/Al$_2$O$_3$, wet-reduced with CH$_2$O in presence of KOH) | 147 | 231 | 84 | 750 |
| 26 (Invention) | F7 (Pd/Ag/Al$_2$O$_3$, wet-reduced with CH$_2$O in presence of RbOH) | 158 | 260 | 102 | 572 |
| 27 (Invention) | F8 (Pd/Ag/Al$_2$O$_3$, wet-reduced with CH$_2$O in presence of CsOH) | 188 | 289 | 101 | 800 |
| 28 (Invention) | F9 (Pd/Ag/Al$_2$O$_3$, wet-reduced with CH$_2$O in presence of KOH) | 146 | 218 | 72 | 1170 |
| 29 (Invention) | F10 (Pd/Ag/Al$_2$O$_3$, wet-reduced with CH$_2$O in presence of RbOH) | 147 | 227 | 80 | 840 |
| 30 | F11 (Pd/Ag/Al$_2$O$_3$, | 158 | 237 | 79 | 670 |

TABLE V-continued

| Run | Catalyst | $T_1$ (°F.) | $T_2$ (°F.) | $T_2-T_1$ | ppm Ethane Formed at $T_1$ |
|---|---|---|---|---|---|
| (Invention) | wet-reduced with $CH_2O$ in presence of CsOH) | | | | |
| 31 (Invention) | F12 (Pd/Ag/Al$_2$O$_3$, wet-reduced with $CH_2O$ in presence of KOH) | 146 | 266 | 120 | 579 |
| 32 (Invention) | F13 (Pd/Ag/Al$_2$O$_3$, wet-reduced with $CH_2O$ in presence of NaOH) | 149 | 203 | 54 | 2350 |
| 33A (Invention) | F14 (Pd/Ag/Al$_2$O$_3$, wet-reduced with $CH_2O$ in presence of KOH) | 145 | 212 | 67 | 1250 |
| 33B (Invention) | F14 (Pd/Ag/Al$_2$O$_3$, wet-reduced with $CH_2O$ in presence of KOH) | 147 | 209 | 62 | 1200 |
| 34 (Invention) | F15 (Pd/Ag/Al$_2$O$_3$, wet-reduced with $CH_2O$ in presence of KOH) | 149 | 237 | 88 | 540 |
| 35 (Invention) | F16 (Pd/Ag/Al$_2$O$_3$, wet-reduced with $CH_2O$ in presence of KOH) | 141 | 241 | 100 | 350 |
| 36 (Invention) | F17 (Pd/Ag/Al$_2$O$_3$, wet-reduced with $CH_2O$ in presence of KOH) | 151 | 238 | 87 | 480 |
| 37 (Invention) | F18 (Pd/Ag/Al$_2$O$_3$, wet-reduced with $CH_2O$, in presence of KF) | 161 | 294 | 133 | 500 |
| 38 (Invention) | F19 (Pd/Ag/Al$_2$O$_3$, wet-reduced with $CH_2O$, in presence of KF + KOH) | 136 | 233 | 97 | 780 |

Test data in Table V clearly show that the reduction of fresh or of used, regenerated Pd/Ag/Al$_2$O$_3$ catalysts with formaldehyde in the presence of an alkali metal compound consistently resulted in higher $T_2-T_1$ values and in lower amounts of ethane formed at the cleanup temperature, $T_1$. Most effective alkali metal compounds were KOH, KF, RbOH and CsOH. Generally, the use of formaldehyde solutions containing 0.002–0.050 mole KOH or RbOH or CsOH or KF were most effective. Additional test data (not included in Table V) indicate that the amounts of ethane produced at temperatures which were 10° F., 20° F. and 30° F., respectively, above the particular "cleanup" temperature were consistently lower in invention runs 22–38 than in control runs 20 and 21. Thus, the wet-reduced, alkali-metal-promoted Pd/Ag/Al$_2$O$_3$ catalysts were more selective to ethylene (rather than ethane) than the untreated catalysts, at comparable conversions of acetylene.

Example VI

This example illustrates wet-reduction of Pd/Ag/Al$_2$O$_3$ catalysts with a dissolved reducing agent other than formaldehyde, in the presence of an alkali metal compound (KOH).

Catalyst G1 (Invention) was prepared essentially in accordance with the procedure for Catalyst F3 (Example V) except an aqueous solution containing 0.03 mole of formic acid and 28.5 grams of water was used as the reducing agent (in lieu of formaldehyde/methanol/water).

Catalyst G2 (Invention) was prepared essentially in accordance with the procedure for Catalyst F3 (Example V) except that an aqueous solution containing 0.03 mole of ascorbic acid (Vitamin C) and 24.7 grams of water was used as the reducing agent (in lieu of formaldehyde/methanol/water).

Catalyst G3 (Invention) was prepared essentially in accordance with the procedure for Catalyst F3 (Example V) except that an aqueous solution containing 0.03 mole of hydrazine hydrate and about 29.0 grams of water was used as the reducing agent (in lieu of formaldehyde/methanol/water).

Catalyst G4 (Invention) was prepared essentially in accordance with the procedure for Catalyst F3 (Example V) except that an aqueous solution containing 0.03 mole of dextrose and 24.6 grams of water was used as the reducing agent (in lieu of formaldehyde/methanol/water).

Catalyst G5 (Invention) was prepared essentially in accordance with the procedure for Catalyst G4 except that 0.003 mole dextrose (in lieu of 0.03 mole dextrose) and 0.025 mole KOH was employed (in lieu of 0.005 mole KOH).

Catalyst G6 (Invention) was prepared essentially in accordance with the procedure for Catalyst G5 except that 0.015 mole KOH was employed (in lieu of 0.025 mole KOH).

Catalyst G7 (Invention) was prepared essentially in accordance with the procedure for Catalyst F3 (Example V) except that a mixture of 0.38 grams of aluminum metal powder, 0.96 grams of KOH and 20 grams of water was used as the reducing agent (in lieu of formaldehyde/methanol/water).

Catalysts G1–G7 were tested substantially in accordance with the procedure used in Example V. Test results are summarized in Table VI.

TABLE VI

| Run | Catalyst | T1 (°F.) | T2 (°F.) | $T_2-T_1$ | ppm Ethane Formed at $T_1$ |
|---|---|---|---|---|---|
| 21 (Control) | F2 (regenerated Pd/Ag/Al$_2$O$_3$, not wet-reduced) | 139 | 176 | 37 | 3950 |
| 39 (Invention) | G1 (Pd/Ag/Al$_2$O$_3$, wet-reduced with formic acid, in presence of KOH) | 137 | 207 | 70 | 894 |
| 40 (Invention) | G2 (Pd/Ag/Al$_2$O$_3$, wet-reduced ascorbic acid, in presence of KOH) | 132 | 216 | 84 | 630 |
| 41 (Invention) | G3 (Pd/Ag/Al$_2$O$_3$, wet-reduced with hydrazine, in presence of KOH) | 138 | 229 | 91 | 550 |
| 42 (Invention) | G4 (Pd/Ag/Al$_2$O$_3$, wet-reduced with dextrose, in presence of KOH) | 143 | 210 | 67 | 1300 |
| 43 (Invention) | G5 (Pd/Ag/Al$_2$O$_3$, wet-reduced with dextrose, in presence of KOH) | 144 | 265 | 121 | 350 |
| 44 (Invention) | G6 (Pd/Ag/Al$_2$O$_3$, wet-reduced with dextrose, in presence of KOH) | 141 | 241 | 100 | 750 |
| 45 (Invention) | G7 (Pd/Ag/Al$_2$O$_3$, wet-reduced with Al, in presence of KOH) | 181 | 298 | 117 | — |

A comparison of the test data in Table VI with those in Table V indicate that the four reducing agents employed in this Example were essentially as effective as formaldehyde, in the presence of potassium hydroxide.

Example VII

This example illustrates that the wet-reduction of supported Pd/Ag catalysts containing inorganic supports other than alumina (namely titania and zirconia) was also quite effective in increasing $T_2-T_1$ values in the selective hydrogenation of acetylene, in accordance with this invention.

Catalyst H1 (Control) was a Pd/Ag/TiO$_2$ catalyst which was prepared by impregnating ⅛ inch, sulfur-free titania pellets with an aqueous palladium(II) nitrate solution (so as to provide a level of about 0.02 weight-% Pd on the TiO$_2$ pellets), drying the Pd/TiO$_2$ particles, calcining them for 8 hours at 400° C. in air, impregnating the calcined Pd/TiO$_2$ particle with an aqueous silver nitrate solution (so as to provide a level of about 0.1 weight-% Ag in the catalyst), drying the Pd/Ag/TiO$_2$ catalyst particles, and then calcining them for 8 hours at 400° C. in air.

Catalyst H2 (Invention) was prepared by soaking Catalyst H1 with a mixture of 26.0 grams of the commercial formaldehyde/methanol/water solution described in Example IV (see preparation of Catalyst E3) and 0.41 grams of 88 weight-% KOH pellets, followed by draining excess solution, drying (at 125° C., for 5 hours) and calcining in air for 2 hours at 400° C.

Both catalysts were tested substantially in accordance with the procedure described in Example I, except that a hydrocarbon-containing feed similar to the one described in Example II was used. Test results are summarized in Table VII.

TABLE VII

| Run | Catalyst | T1 (°F.) | T2 (°F.) | T2–T1 | ppm Ethane Formed at $T_1$ |
|---|---|---|---|---|---|
| 46 (Control) | H1 (Pd/Ag/TiO$_2$, not wet-reduced | 127 | 167 | 40 | 3900 |
| 47 (Invention) | H2 (Pd/Ag/TiO$_2$, wet-reduced with CH$_2$O in presence of KOH | 126 | 191 | 65 | 1100 |

Test data in Table VII clearly show that wet-reduction of Pd/Ag/TiO$_2$ had essentially the same beneficial effects as wet-reduction of Pd/Ag/Al$_2$O$_3$ (described in previous examples).

Additional preliminary tests (not described in detail herein) indicate that the use of a Pd/Ag/ZrO$_2$ catalyst (which had not been wet-reduced in the selective hydrogenation of acetylene) was almost as effective (in terms of $T_2-T_1$ values) as Pd/Ag/Al$_2$O$_3$ catalysts (also not wet-reduced). Based on these preliminary test results, it is concluded that the wet-reduction of Pd/Ag/ZrO$_2$ catalysts, with or without the presence of alkali metal compounds, in accordance with this invention will produce catalysts exhibiting enhanced $T_2-T_2$ values and higher selectivities to ethylene (as compared with the untreated catalysts). Example VIII This example illustrates a method of preparing an effective acetylene hydrogenation catalyst by wet-reduction and subsequent promotion with potassium fluoride.

Catalyst I (Invention) was prepared by soaking 23.3 grams of Catalyst B 1 ("G-83C", described in Example I) in 30 cc of a 37 weight-% formaldehyde solution (described in Example III for Catalyst D2), adding about 0.5 gram solid KOH to the catalyst/solution mixture, stirring this mixture for 30 minutes at room temperature, adding again about 0.5 gram of solid KOH, and stirring the obtained mixture again for about 30 minutes at room temperature. Thereafter, excess liquid was drained, and the soaked, wet-reduced mixture was washed twice with fresh methanol and then twice with distilled water (so as to remove substantially all KOH which had been incorporated into the catalyst). The washed, wet-reduced catalyst was dried overnight at 180° F., and then soaked with a solution of 0.355 gram anhydrous potassium fluoride in 7.58 grams of water. The KF-impregnated catalyst was dried overnight at 180° F. and calcined for 1.5 hours in air at 370° C.

The thus obtained catalyst, which contained about 1 weight-% K (as fluoride), was tested for its acetylene hydrogenation activity substantially in accordance with the procedure described in Example I. Result: $T_1$ was 154° F., $T_2$ was 245° F., and $T_2-T_1$ was 91° F.

Thereafter, the catalyst was exposed to the feed at "runaway" conditions, i.e., at a temperature in excess of 245° F., for about 22 minutes, so as to simulate possible damage to the catalyst by a "runaway" reaction in a plant operation. Then the catalyst was tested again (after lowering the temperature of the reactor while $H_2$ gas passed through). Result: $T_1$ was 161° F., $T_2$ was 259° F., and $T_2-T_1$ was 98° F. This result clearly indicates that no adverse effect on the KF-promoted, wet-reduced Pd/Ag/$Al_2O_3$ catalyst had occurred by this exposure to "runaway" conditions.

Reasonable variations, modifications and adaptations for various usages and conditions can be made within the scope of the disclosure and the appended claims, without departing from the scope of this invention.

That which is claimed is:

1. In a process for the selective hydrogenation of acetylene to ethylene which comprises mixing (a) a feed gas comprising acetylene and (b) hydrogen gas and contacting the mixture of (a) and (b) with (c) an effective catalyst composition, the improvement which comprises employing a catalyst composition which has been prepared by a method consisting essentially of the steps of:

(1) contacting a solid composition comprising palladium, silver and an inorganic support material with a liquid reduction composition comprising (i) at least one reducing agent selected from the group consisting of alkali metal borohydrides, hydrazine, aldehydes containing 1–6 carbon atoms per molecule, ketones containing 1–6 carbon atoms per molecule, carboxylic acids containing 1–6 carbon atoms per molecule, aluminum metal and zinc metal, (ii) at least one non-reducing liquid component, and (iii) at least one dissolved alkali metal compound selected from the group consisting of alkali metal hydroxides and alkali metal fluorides, at a temperature of up to about 60° C. for a time period of at least about 1 second, so as to produce a wet-reduced solid composition;

(2) substantially separating said wet-reduced solid composition produced in step (1) from said liquid reduction composition; and (3) drying the substantially separated, wet-reduced solid composition obtained in step (2).

2. A process in accordance with claim 1, wherein said inorganic support material is selected from the group consisting of alumina, titania, zirconia and mixtures thereof; said at least one reducing agent is selected from the group consisting of sodium borohydride, potassium borohydride, hydrazine, formaldehyde, formic acid, ascorbic acid and aluminum metal; said at least one non-reducing liquid component is selected from the group consisting of water, methanol and mixtures thereof; said at least one dissolved alkali metal compound is selected from the group consisting of potassium hydroxide, potassium fluoride, rubidium hydroxide, rubidium fluoride, cesium hydroxide and cesium fluoride; said temperature is about 10°–60° C.; and said time period is about 10 seconds to about 10 hours.

3. A process in accordance with claim 2, wherein said temperature in step (1) is about 20°–50° C., said time period of step (1) is about 0.02–2 hours, and the pressure in step (1) is approximately atmospheric.

4. A process in accordance with claim 2 wherein said solid composition used in step (1) contains about 0.01–0.2 weight-% palladium, about 0.02–2 weight-% silver, and alumina as the inorganic support material.

5. A process in accordance with claim 4, wherein said at least one reducing agent used in step (1) is selected from the group consisting of sodium borohydride and potassium borohydride.

6. A process in accordance with claim 4, wherein said at least one reducing agent is hydrazine, and said at least one dissolved alkali metal compound is selected from the group consisting of potassium hydroxide, potassium fluoride, rubidium hydroxide and cesium hydroxide.

7. A process in accordance with claim 4, wherein said at least one reducing agent used in step (1) is formaldehyde, and said at least one dissolved alkali metal compound is selected from the group consisting of potassium hydroxide, potassium fluoride, rubidium hydroxide and cesium hydroxide.

8. A process in accordance with claim 4, wherein said at least one reducing agent used in step (1) is selected from the group consisting of formic acid and ascorbic acid, and said at least one dissolved alkali metal compound is selected from the group consisting of potassium hydroxide, potassium fluoride, rubidium hydroxide and cesium hydroxide.

9. A process in accordance with claim 4, wherein said at least one reducing agent used in step (1) is aluminum metal powder, and said at least one dissolved alkali metal compound is selected from the group consisting of potassium hydroxide, potassium fluoride, rubidium hydroxide and cesium hydroxide.

10. A process in accordance with claim 1, wherein the weight percentage of said at least one reducing agent in said liquid reduction composition is employed in step (1) is about 0.5–50 weight-%.

11. A process in accordance with claim 1, wherein said feed gas comprises acetylene as an impurity in an ethylene stream, at an acetylene concentration of about 1–50,000 ppm.

12. A process in accordance with claim 1, wherein said selective hydrogenation is carried out at a temperature of about 0° C. to about 150° C. and a pressure of about 100 to about 1,000 psig.

13. In a process for the selective hydrogenation of acetylene to ethylene which comprises mixing (a) a feed gas comprising acetylene and (b) hydrogen gas and contacting the mixture of (a) and (b) with (c) an effective catalyst composition, the improvement which comprises employing a catalyst composition which has been prepared by a method consisting essentially of the steps of:

(1) contacting (a) a solid composition comprising palladium, silver and an inorganic support material with (b) a liquid reduction composition comprising (i) at least one reducing agent selected from the group consisting of alkali metal borohydrides, hydrazine, aldehydes containing 1–6 carbon atoms per molecule, ketones containing 1–6 carbon atoms per molecule, carboxylic acids containing 1–6 carbon atoms per molecule, sugars containing an aldehyde group, sugars containing an α-hydroxyketone group, aluminum metal and zinc metal, (ii) at least one non-reducing liquid component, and (iii) at least one dissolved alkali metal compound selected from the group consisting of alkali metal hydroxides and alkali metal fluorides, at a temperature of up to about 60° C. for a time period of at least about 1 second, so as to produce a wet-reduced, solid composition;

(2) substantially separating the wet-reduced solid composition produced in step (1) from said liquid reduction composition;

(3) drying the substantially separated, wet-reduced solid composition obtained in step (2); and (4) heating the dried, wet-reduced solid composition obtained in step (3) in an oxidizing gas atmosphere at a temperature of about 300°–700° C. for a time period of at least about 10 minutes.

14. A process in accordance with claim 13, wherein said inorganic support material is selected from the group consisting of alumina, titania and zirconia; said at least one reducing agent is selected from the group consisting of sodium borohydride, potassium borohydride, hydrazine, formaldehyde, formic acid, ascorbic acid, dextrose and aluminum metal; said at least one non-reducing liquid component is selected from the group consisting of water, methanol and mixtures thereof; said at least one dissolved alkali metal is selected from the group consisting of potassium hydroxide, potassium fluoride, rubidium hydroxide, rubidium fluoride, cesium hydroxide and cesium fluoride; said temperature in step (1) is about 10°–60° C.; and said time period in step (1) is about 10 seconds to about 10 hours.

15. A process in accordance with claim 14, wherein said temperature in step (1) is about 20°–50° C., said time period of step (1) is about 0.02–2 hours, and the pressure in step (1) is about atmospheric.

16. A process in accordance with claim 14, wherein said solid composition used in step (1) contains about 0.01–0.2 weight-% palladium, about 0.02–2 weight-% silver, and alumina as the inorganic support material.

17. A process in accordance with claim 16, wherein said at least one reducing agent is selected from the group consisting of sodium borohydride and potassium borohydride.

18. A process in accordance with claim 16, wherein said at least one reducing agent is hydrazine, and said at least one dissolved alkali metal compound is selected from the group consisting of potassium hydroxide, potassium fluoride, rubidium hydroxide and cesium hydroxide.

19. A process in accordance with claim 16, wherein said at least one reducing agent is formaldehyde, and said at least one dissolved alkali metal compound is selected from the group consisting of potassium hydroxide, potassium fluoride, rubidium hydroxide and cesium hydroxide.

20. A process in accordance with claim 16, wherein said at least one reducing agent is selected from the group consisting of formic acid and ascorbic acid, and said at least one dissolved alkali metal compound is selected from the group consisting of potassium hydroxide, potassium fluoride, rubidium hydroxide and cesium hydroxide.

21. A process in accordance with claim 16 wherein said at least one reducing agent is dextrose, and said at least one dissolved alkali metal compound is selected from the group consisting of potassium hydroxide, potassium fluoride, rubidium hydroxide and cesium hydroxide.

22. A process in accordance with claim 16, wherein said at least one reducing agent is aluminum metal powder, and said at least one dissolved alkali metal compound is selected from the group consisting of potassium hydroxide and potassium fluoride.

23. A process in accordance with claim 13, wherein the weight percentage of said at least one reducing agent in said liquid reduction composition employed in step (1) is about 0.5–50 weight-%.

24. A process in accordance with claim 13, wherein said feed gas comprises acetylene as an impurity in an ethylene stream at an acetylene concentration of about 1–50,000 ppm.

25. A process in accordance with claim 13, wherein said selective hydrogenation is carried out at a temperature of about 0° C. to about 150° C. and a pressure of about 100 to about 1,000 psig.

26. A process in accordance with claim 13, wherein step (4) is carried out in air at a temperature of about 400°–600° C. for a time period of about 0.2–20 hours.

* * * * *